United States Patent
Huang et al.

(10) Patent No.: US 12,016,730 B2
(45) Date of Patent: Jun. 25, 2024

(54) ULTRASONIC IMAGING OF ACOUSTIC ATTENUATION COEFFICIENTS WITH CONFIDENCE ESTIMATION

(71) Applicant: KONINKLIJKE PHILIPS N.V., Eindhoven (NL)

(72) Inventors: Sheng-Wen Huang, Ossining, NY (US); Hua Xie, Cambridge, MA (US); Man M. Nguyen, Melrose, MA (US); Carolina Amador Carrascal, Everett, MA (US); Jean-Luc Francois-Marie Robert, Cambridge, MA (US); Vijay Thakur Shamdasani, Kenmore, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 319 days.

(21) Appl. No.: 17/420,821

(22) PCT Filed: Jan. 20, 2020

(86) PCT No.: PCT/EP2020/051208
§ 371 (c)(1),
(2) Date: Jul. 6, 2021

(87) PCT Pub. No.: WO2020/152066
PCT Pub. Date: Jul. 30, 2020

(65) Prior Publication Data
US 2022/0087653 A1    Mar. 24, 2022

Related U.S. Application Data

(60) Provisional application No. 62/796,372, filed on Jan. 24, 2019.

(51) Int. Cl.
*A61B 8/00*    (2006.01)
*A61B 8/08*    (2006.01)
*G01S 7/52*    (2006.01)

(52) U.S. Cl.
CPC ............ *A61B 8/5253* (2013.01); *A61B 8/463* (2013.01); *A61B 8/5207* (2013.01);
(Continued)

(58) Field of Classification Search
CPC ............ G01S 7/52071; G01S 7/52036; A61B 8/5207; A61B 8/463; A61B 8/5253; A61B 8/488; H04N 13/0282
See application file for complete search history.

(56) References Cited

U.S. PATENT DOCUMENTS 5,482,045 A    1/1996    Rust et al.
5,627,906 A    5/1997    Walach
(Continued)

FOREIGN PATENT DOCUMENTS

WO    2018237244 A1    12/2018
WO    WO-2018237244 A1 *    12/2018    ........... A61B 8/5223

OTHER PUBLICATIONS

Insana (NPL; Improvements in the spectral difference method for measuring ultrasonic attenuation; May 29, 2014) (Year: 2014).*
(Continued)

*Primary Examiner* — Daniel L Murphy
*Assistant Examiner* — Amie M Ndure

(57) ABSTRACT

An ultrasound system produces maps of acoustic attenuation coefficients from pulse echo signals. Maps are produced using different attenuation coefficient or slope estimation methods, and a plurality of maps from different estimation methods are compounded to produce a final attenuation coefficient map. Confidence maps may also be produced for one or more attenuation coefficient maps, and the confidence
(Continued)

map displayed or its measures used to determine weighting for the compounding process.

13 Claims, 3 Drawing Sheets

(52) U.S. Cl.
CPC ...... *G01S 7/52036* (2013.01); *G01S 7/52071* (2013.01); *A61B 8/488* (2013.01)

(56) References Cited

U.S. PATENT DOCUMENTS

| | | | |
|---|---|---|---|
| 5,883,613 A | 3/1999 | Iwaki | |
| 5,997,479 A | 12/1999 | Savord et al. | |
| 6,013,032 A | 1/2000 | Savord | |
| 6,330,885 B1 | 12/2001 | Weissman et al. | |
| 6,623,432 B2 | 9/2003 | Powers et al. | |
| 11,619,728 B2 * | 4/2023 | McLaughlin | A61B 8/5269 600/442 |
| 2004/0264627 A1 * | 12/2004 | Besson | A61B 6/4241 378/5 |
| 2014/0029817 A1 | 1/2014 | Gleichman et al. | |
| 2015/0071516 A1 * | 3/2015 | Kim | G01S 7/5202 382/131 |
| 2020/0146656 A1 * | 5/2020 | Gong | G01S 15/892 |
| 2020/0256971 A1 * | 8/2020 | Huang | G01S 7/5202 |

OTHER PUBLICATIONS

Andres (NPL; Regularized Spectral Log Difference Technique for Ultrasonic Attenuation Imaging; Mar. 3, 2018) (Year: 2018).*

Elbakri (NPL; Segmentation-free statistical image reconstruction for polyenergetic x-ray computed tomography with experimental validation; Jul. 22, 2003) (Year: 2003).*

Schreibmann (NPL; MR-based attenuation correction for hybrid PET-MR brain imaging systems using deformable image registration; Apr. 21, 2010) (Year: 2010).*

PCT/EP2020/051208 ISR & WO, Apr. 1, 2020, 16 Page Document.

Jenderka: "Resolution Improved Ultrasound Attenuation Estimation Based on rf-Data of Spatial Compound Scans"; 2004 IEEE Internationalultrasonics, Ferroelectrics, and Frequency Control Joint 50th Anniversary Conference, pp. 2078-2091.

Karamalis et al: "Ultrasound Confidence Maps Using Random Walks"; Medical Image Analysis 16 (20120 pp. 1101-1112.

Klimonda et al: "Tissue Attenuation Estimation by Mean Frequency Downshift and Bandwidth Limitation"; IEEE Transactions on Ultrasonics, Ferroelectrics, and Frequency Control, vol. 63, No. Aug. 8, 2016, pp. 1107-1115.

Labyed et al: "A Theoretical Comparison of Attenuation Measurement Techniques From Backscattered Dultrasound Echoes"; 2011 Acoustical Society of America, pp. 2316-2324.

Samimi et al: "Optimum-Diffraction-Corrected Frequency-Shift Estimator of the Ultrasonic Attenuation Coefficient"; IEEE Transactions on Ultrasonics, Ferroelectrics, and Frequency Control, vol. 63, No. 5, May 2016.

Walach et al: "Local Tissue Attenuation Images Based on Pulsed-Echo Ultrasound Scans"; IEEE Transactions on Biomedical Engineering, vol. 36, No. 2, Feb. 1989, pp. 211-221.

* cited by examiner

ULTRASONIC IMAGING OF ACOUSTIC ATTENUATION COEFFICIENTS WITH CONFIDENCE ESTIMATION

CROSS-REFERENCE TO PRIOR APPLICATIONS

This application is the U.S. National Phase application under 35 U.S.C. § 371 of International Application No. PCT/EP2020/051208, filed on Jan. 20, 2020, which claims the benefit of U.S. Provisional Patent Application No. 62/796,372, filed on Jan. 24, 2019. These applications are hereby incorporated by reference herein.

This invention relates to ultrasound imaging systems and, in particular, to the imaging of acoustic attenuation coefficient maps with confidence estimation.

Pulse-echo ultrasound imaging systems transmit beams of acoustic energy over an image field. As each transmitted beam encounters acoustic reflectors and tissue boundaries, some of the transmitted energy is reflected back to the transmitting transducer and received as an echo. In this way, a sequence of echoes is received from progressively deeper tissues as the ultrasound beam energy travels deeper into the body. The amplitudes of the echoes are detected and displayed in correspondence with their times of reception, which correspond to the depths from which they were received. The display thereby reveals characteristics of the structure of the tissue within the body. But the beam energy is continually attenuated as it travels through the tissue and encounters acoustic scatterers along the paths of the beams. This attenuation will result in the reception of generally stronger echoes from tissue in the near field, and generally weaker echoes from tissue at greater depths. Without compensation for this effect, the resulting image will appear brighter in the near field (from higher amplitude echoes) and darker in the far field due to the reception of lower echo amplitudes. The common compensation for this effect is time gain control (TGC), whereby the receiver increases the amplification of echo signals as they are received from progressively greater depths. Ultrasound systems are equipped with TGC settings which enable the user to select the gain applied at different depths, from which the ultrasound system computes a TGC curve for continual gain variation during echo reception. Ultrasound systems are also commonly equipped with pre-determined TGC curves which experience has shown are nominal for different tissue types. Thus, a user can call up a nominal TGC curve for the liver for an abdominal exam, or a different nominal TGC curve when imaging the breast.

While nominal curves may provide an average characteristic of particular tissue types, they are unable to further differences each particular tissue type, e.g. the attenuation differences from one person to another by reason of tissue density, composition, location differences, and other properties. It would thus be desirable to know the attenuation characteristics of the specific tissue being diagnosed, rather than rely upon a nominal or average characteristic. Accordingly, efforts have been directed toward measuring the attenuation characteristics for a subject in vivo by estimating and displaying the degree of attenuation for each point in an ultrasound image field. See, e.g., "Local Tissue Attenuation Images Based on Pulsed-Echo Ultrasonic Scans" by Walach et al., *IEEE Trans. On Biomedical Engineering*, vol. BME-33, no. 7, July 1986 at pp 637-43. Walach et al. propose that such maps of local attenuation in an image field can be used to pinpoint tissue pathology by reason of its different attenuation characteristic from that of healthy tissue.

The estimations used to produce such attenuation maps, however, are generally dependent upon certain assumptions made concerning tissue, such as the local homogeneity of tissue, which may not be the case throughout the image field. Other sources of error include the effects of frequency-dependent acoustic diffraction due to aberration, speckle, aperture obstruction, clutter, or other adverse conditions. Thus, it would be desirable to produce maps of acoustic attenuation in an image field which are less subject to such error sources.

In accordance with the principles of the present invention, an ultrasound imaging system and signal processing technique are described for more accurately estimating acoustic attenuation coefficients over an ultrasound image field. The inventive system and technique utilize different techniques to produce different attenuation coefficient maps for an image field. The different maps are then compounded to produce a final attenuation coefficient map. A confidence measure of the estimated reliability of each map and its local attenuation coefficients may be used when combining the individual maps for greater accuracy.

Figure 1:
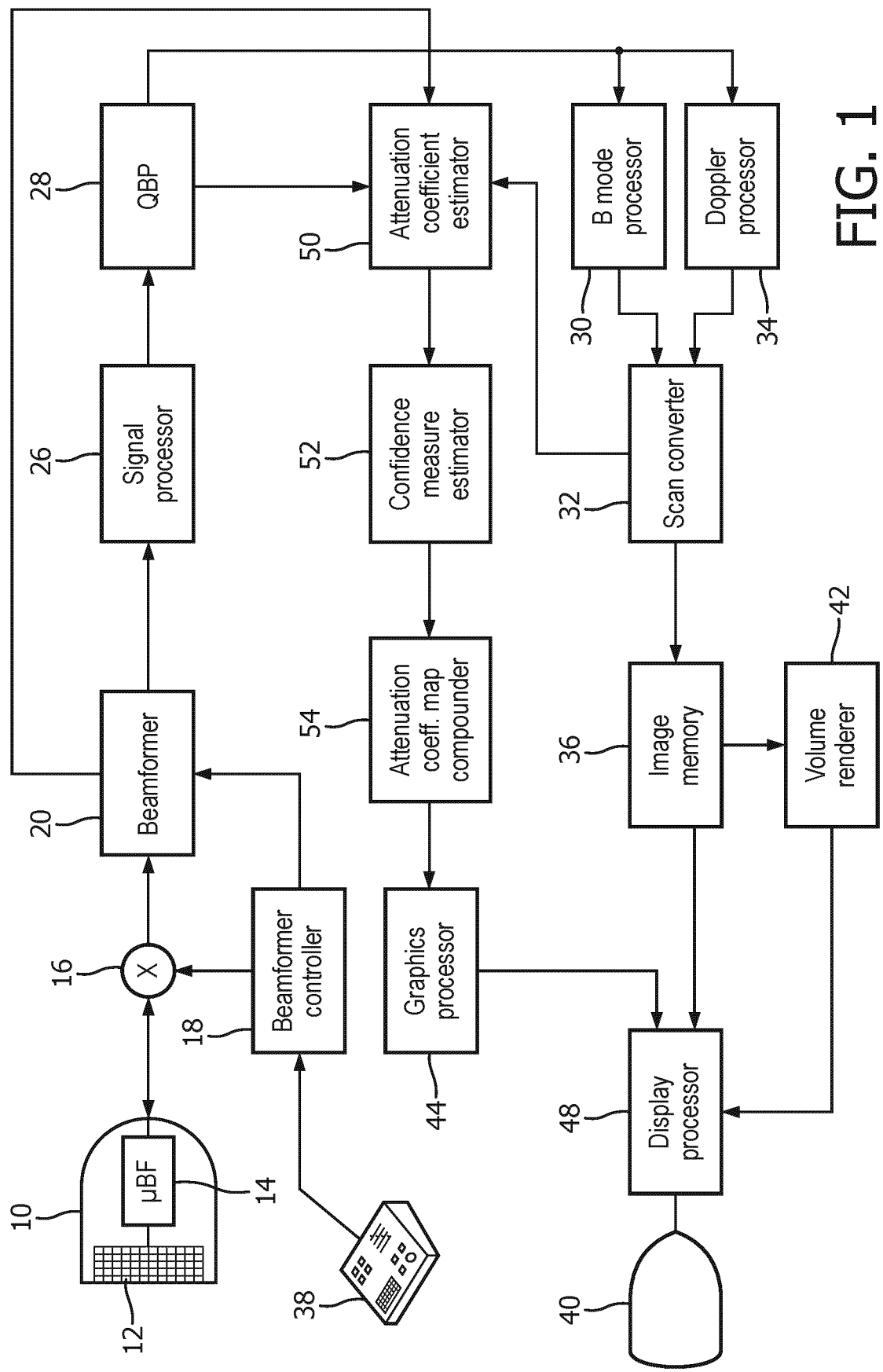
FIG. 1 illustrates in block diagram form an ultrasound system configured in accordance with the principles of the present invention.

Referring now to FIG. 1, an ultrasonic diagnostic imaging system constructed in accordance with the principles of the present invention is shown in block diagram form. A transducer array 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation (in 3D) and azimuth. The transducer array 12 is coupled to an optional microbeamformer 14 in the probe which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 12 under control of the microbeamformer 14 is directed by a beamformer controller 18 coupled to the T/R switch and the main beamformer 20, which receives input from the user's operation of the user interface or control panel 38. Among the transmit characteristics controlled by the transmit controller are the number, spacing, amplitude, phase, frequency, polarity, and diversity of transmit waveforms. Beams formed in the direction of pulse transmission may be steered straight ahead from the transducer array, or at different angles on either side of an unsteered beam for a wider sector field of view. For some applications, unfocused plane waves may be used for transmission. Most 1D array probes of relatively small array length, e.g., a 128-element array, do not use a microbeamformer but are driven and respond directly to the main beamformer.

The echoes received by a contiguous group of transducer elements are beamformed by appropriately delaying them and then combining them. The partially beamformed signals produced by the microbeamformer 14 from each patch are coupled to the main beamformer 20 where partially beamformed signals from individual patches of transducer elements are combined into a fully beamformed coherent echo signal, or echo signals from elements of a one-dimensional array without a microbeamformer are combined. For example, the main beamformer 20 may have 128 channels, each of which receives a partially beamformed signal from a patch of 12 transducer elements, or from an individual element. In this way the signals received by over 1500 transducer elements of a two-dimensional array transducer can contribute efficiently to a single beamformed signal, and signals received from an image plane are combined.

The microbeamformer 14 or the beamformer 20 also include amplifiers which amplify the signals received from each element or patch of the transducer array 12. These amplifiers have controllable gain characteristics, which are controlled by a TCG curve stored in the ultrasound system, TGC controls on the user interface 38, or a combination of both. See, e.g., U.S. Pat. No. 5,482,045 (Rust et al.) Beamformation by delaying and summing signals from individual transducer elements or patches is thus performed with echo signals that have undergone time gain control compensation.

The coherent echo signals undergo signal processing by a signal processor 26. This processing may include compounding and/or filtering. In certain embodiments, filtering includes application of one or more filters, including digital filters. w. The filtered echo signals may be coupled to a quadrature bandpass filter (QBP) 28. The QBP performs three functions: band limiting the RF echo signal data, producing in-phase and quadrature pairs (I and Q) of echo signal data, and decimating the digital sample rate. The QBP comprises two separate filters, one producing in-phase samples and the other producing quadrature samples, with each filter being formed by a plurality of multiplier-accumulators (MACs) implementing an FIR filter. The signal processor can also shift the frequency band to a lower or baseband frequency range, as can the QBP. The digital filter of the signal processor 26 can be a filter of the type disclosed in U.S. Pat. No. 5,833,613 (Averkiou et al.), for example.

Compounding may be accomplished using one or more techniques known in the art. Compounding may involve averaging envelop/magnitude, with or without log compression. Typically compounding occurs after the QBP.

Figure 3A:
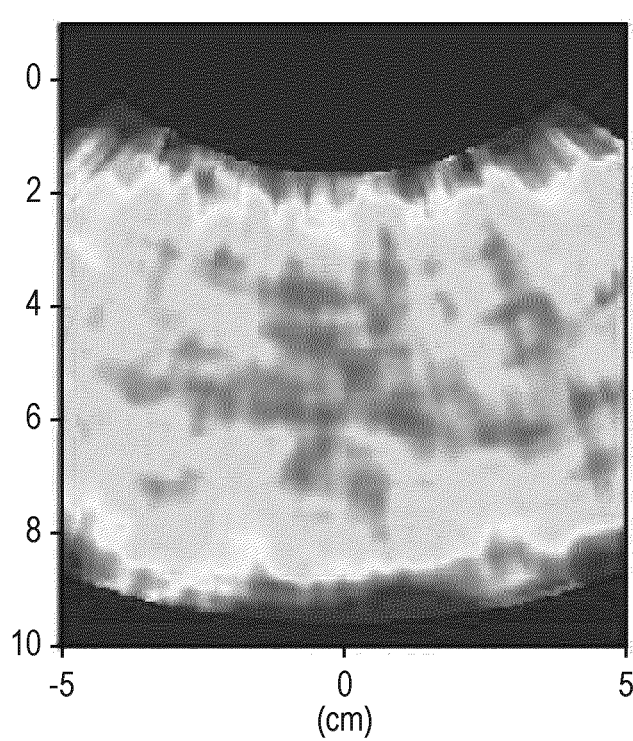
FIGS. 3a and 3b illustrate confidence maps for attenuation coefficient maps of image fields with different acoustic scatterer characteristics.
Figure 3B:
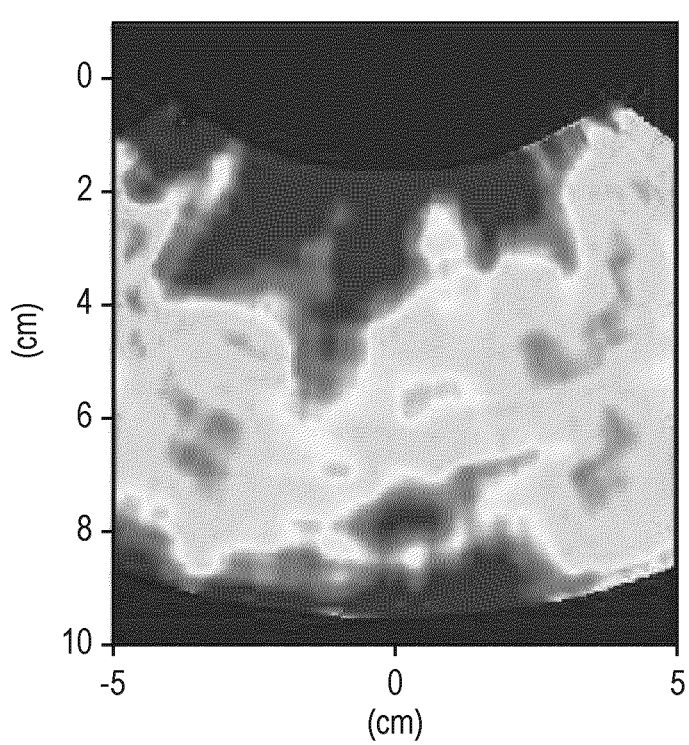

The beamformed and processed coherent echo signals are coupled to a B mode processor 30 which produces signals for a B mode image of structure in the body such as tissue. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 34. The Doppler processor 34 stores ensembles of echo signals from discrete points in an image field which are then used to estimate the Doppler shift at points in the image with a fast Fourier transform (FFT) processor. The rate at which the ensembles are acquired determines the velocity range of motion that the system can accurately measure and depict in an image. The Doppler shift is proportional to motion at points in the image field, e.g., blood flow and tissue motion. For a color Doppler image, the estimated Doppler flow values at each point in a blood vessel are wall filtered and converted to color values using a look-up table. The wall filter has an adjustable cutoff frequency above or below which motion will be rejected such as the low frequency motion of the wall of a blood vessel when imaging flowing blood. The B mode image signals and the Doppler flow values are coupled to a scan converter 32 which converts the B mode and Doppler samples from their acquired R-θ coordinates to Cartesian (x,y) coordinates for display in a desired display format, e.g., a rectilinear display format or a sector display format. Either the B mode image or the Doppler image may be displayed alone, or the two shown together in anatomical registration in which the color Doppler overlay shows the blood flow in tissue and vessels in the image as shown in FIGS. 3a-3b. Another display possibility is to display side-by-side images of the same anatomy which have been processed differently. This display format is useful when comparing images.

The scan converted image is coupled to an image data memory 36, where it is stored in memory locations addressable in accordance with the spatial locations from which the image values were acquired. Image data from 3D scanning can be accessed by a volume renderer 42, which converts the echo signals of a 3D data set into a projected 3D image as viewed from a given reference point as described in U.S. Pat. No. 6,530,885 (Entrekin et al.) The 3D images produced by the volume renderer 42 and 2D images produced by the scan converter 32 are coupled to a display processor 48 for further enhancement, buffering and temporary storage for display on an image display 40.

In accordance with the principles of the present invention, the ultrasound system of FIG. 1 includes a subsystem which produces image maps of acoustic attenuation coefficient estimates. The subsystem includes an attenuation coefficient estimator 50. The attenuation coefficient estimator may generate coefficient maps from beamformed data (output of 20), QBD filtered data (output of 28), or from scan converted image data (output of 32). Typically the input is either RF or IQ data. The attenuation coefficient estimator is capable of producing different attenuation coefficient maps using different methods of coefficient estimation. The coefficient estimation processor operates on RF (or I/Q) values in conjunction with a map of reference values, such as RF data from a homogeneous tissue phantom, a theoretical model of power spectra, or a numerical simulation of power spectra. The reference value map is stored in the attenuation coefficient estimator or in a memory accessible by the attenuation coefficient estimator.

The different attenuation coefficient maps produced by the attenuation coefficient estimator are coupled to a confidence measure estimator 52, which produces spatially corresponding maps of estimate confidence, either of a single attenuation coefficient map or of one attenuation coefficient map in relation to another. Although it is understood that in some instances the attenuation coefficient estimator 50 and the confidence measure estimator 52 may be the same or different process, as the confidence level is a by-product of the attenuation co-efficient estimation process). The attenuation coefficient maps and the results of the confidence estimations are coupled to an attenuation coefficient map compounder 54, which compounds (combines) the coefficient map values on a pixel-by-pixel basis, such as by weighted averaging, where the weighting is determined by the confidence estimations. The result is a final attenuation coefficient map produced by not a single estimation method, but from a combination of several estimation techniques, and which takes into consideration the reliability of the different techniques as indicated by the confidence estimations. The final attenuation coefficient map is coupled to a graphics processor 44 which formats the map for display, as by color-coding the coefficient values of the map in relation to a range of scaled color values. The attenuation coefficient map is coupled to the display processor 48 for display on the image display 40. Optionally, the confidence estimation map may also be displayed in the same manner, so that the user can assess the reliability of attenuation estimates made in a particular region of interest (ROI) of the image field.

The processor of the attenuation coefficient estimator 50 can use any of a number of techniques for estimating acoustic attenuation coefficient values over an image field, three of which are described below. They are the spectral difference method, the spectral log difference method, and the maximum likelihood method, such as those described in Y. Labyed and T. A. Bigelow, "A theoretical comparison of attenuation measurement techniques from backscattered ultrasound echoes," J. Acoust. Soc. Am., vol. 129, no. 4, pp. 2316-2324, 2011, incorporated by reference herein. Estimation of acoustic attenuation coefficients (in units of dB/cm or its equivalents) or acoustic attenuation coefficient slope (in units of dB/cm/MHz or its equivalents) from pulse echo signals can be based on the following expressions:

$$S_s(f,z) = P(f)D_s(f,z)A_s(f,z_0)B_s(f,z)\exp[-4\alpha_s(f)(z-z_0)], \quad [1]$$

and $$S_r(f,z) = P(f)D_r(f,z)A_r(f,z_0)B_r(f,z)\exp[-4\alpha_r(f)(z-z_0)], \quad [2]$$

where the subscripts s and r denote tissue sample and reference, respectively; f is frequency; z is depth in the image field; S(f,z) is a measured power spectrum from a region of interest (ROI) centered at depth z; P(f) is transducer response combined with the spectrum of the transmitted pulses; D(f,z) is diffraction effects; $z_0$ is the starting depth of the ROI; $A(f,z_0)$ is the cumulative attenuation effects from the transducer surface to depth $z_0$; B(f,z) is the effects of acoustic scattering; and $\alpha(f)$ is the attenuation coefficient in the ROI. By using $S_r(f,z)$ from a homogeneous reference phantom and assuming the same speed of sound for the tissue sample and the reference, P(f) and $D_s(f,z)$ are suppressed and the following expression will hold:

$$RS(f,z) \equiv \frac{S_s(f,z)}{S_r(f,z)} \cong \frac{A_s(f,z_0)B_s(f,z)}{A_r(f,z_0)B_r(f)}\exp\{-4(z-z_0)[\alpha_s(f)-\alpha_r(f)]\}. \quad [3]$$

From these starting relationships, the three methods for estimating attenuation coefficients over an image field can be computed as follows.

A. The Spectral Difference Method.

The spectral difference method assumes that the term $$\frac{A_s(f,z_0)B_s(f,z)}{A_r(f,z_0)B_r(f)}$$

in expression [3] above is independent of z. Accordingly, $$\ln\left[\frac{S_s(f,z)}{S_r(f,z)}\right] \cong -4(z-z_0)[\alpha_s(f)-\alpha_r(f)] + G(f), \quad [4]$$

where $$G(f) = \ln\left[\frac{A_s(f,z_0)B_s(f)}{A_r(f,z_0)B_r(f)}\right],$$

and $\alpha_s(f)$ at a given frequency f can be obtained through estimating the slope of ln $$\left[\frac{S_s(f,z)}{S_r(f,z)}\right]$$

with respect to z. Note that the attenuation coefficient of the reference, $\alpha_r(f)$, is known. In soft tissue $\alpha$ can be modelled as $$\alpha(f) = \beta f^n. \quad [5]$$

When it is assumed that n=1, then $\alpha_r(f)=\beta_r f$, and $\alpha_s(f)=\beta_s f$, and $$\ln\left[\frac{S_s(f,z)}{S_r(f,z)}\right] \cong -4(z-z_0)(\beta_s - \beta_r)f + G(f). \quad [6]$$

Figure 2A:
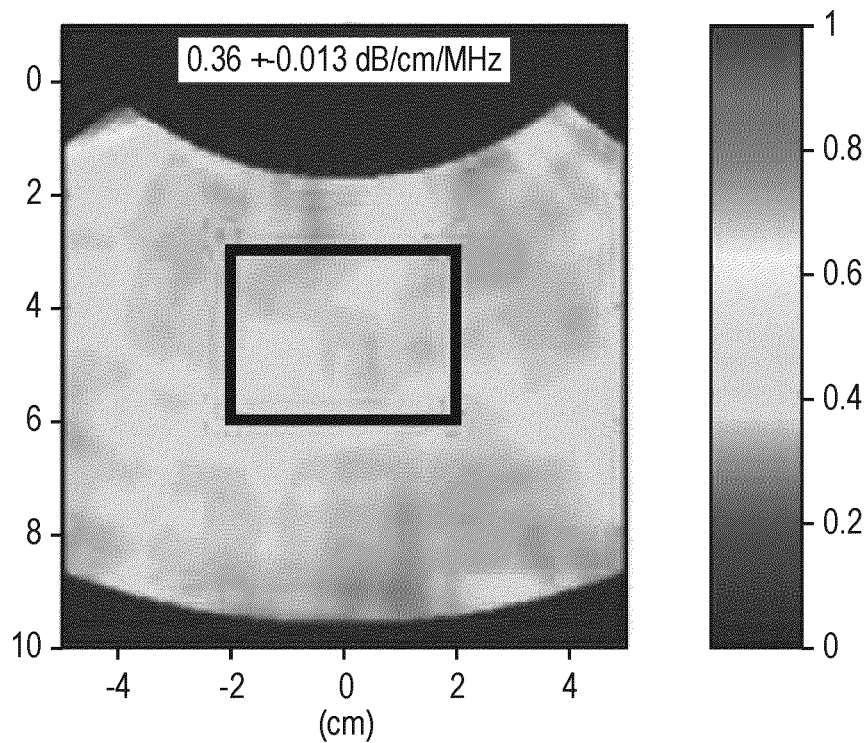
FIGS. 2a and 2b illustrate attenuation coefficient maps obtained using the spectral difference method and the maximum likelihood method, respectively.

The attenuation coefficient slope $\beta_s$ can then be estimated as $$\beta_s \cong \beta_r - \frac{1}{4}\frac{d}{dz}\left(\frac{\int_{f_1}^{f_2}\left[\frac{w(f)}{f}\right]\ln\left[\frac{S_s(f,z)}{S_r(f,z)}\right]df}{\int_{f_1}^{f_2}w(f)df}\right), \quad [7]$$

where w(f) is a weighting function. Note that the effects of G(f), assuming the scattering effects $B_s$ are independent of depth z, vanish after the differentiation with respect to z. When the assumption of depth independence of scattering is valid, the spectral difference method usually outperforms other methods such as the maximum likelihood (ML) method described below. An attenuation coefficient slope map produced by the spectral difference method when this assumption holds is illustrated in FIG. 2a.

B. The Spectral Log Difference Method.

An implementation of this method begins with the assumption that the effects of acoustic scattering at one depth of tissue are related to the effects at another depth by a constant. That is, $B_s(f,z_2)=cB_s(f,z_1)$, where c is a constant. Then $$\ln\left[\frac{S_s(f,z_2)}{S_r(f,z_2)}\right] - \ln\left[\frac{S_s(f,z_1)}{S_r(f,z_1)}\right] \cong -4(z_2-z_1)[\alpha_s(f)-\alpha_r(f)] + \ln[c], \quad [8]$$

where again the attenuation coefficient of the reference $\alpha_r(f)$ is known. By considering the tissue model in [5] again, this leads to $$\ln\left[\frac{S_s(f,z_2)}{S_r(f,z_2)}\right] - \ln\left[\frac{S_s(f,z_1)}{S_r(f,z_1)}\right] \cong -4(z_2-z_1)[\beta_s f^n - \alpha_r(f)] + \ln[c], \quad [9]$$

which is a function of frequency f. The three unknowns, the attenuation coefficient slope $\beta_s$, n, and ln[c], can then be estimated by curving fitting. Exemplifications of this technique may be found at Y. Labyed and T. A. Bigelow, "A theoretical comparison of attenuation measurement techniques from backscattered ultrasound echoes," J. Acoust. Soc. Am., vol. 129, no. 4, pp. 2316-2324, 2011.

C. The Maximum Likelihood Method.

This method begins by assuming that n=1 in expression [9]. Then $\alpha_r(f) = \beta_r f$ and $\alpha_s(f) = \beta_s f$, and expression [9] becomes $$\ln\left[\frac{S_s(f, z_2)}{S_R(f, z_2)}\right] - \ln\left[\frac{S_s(f, z_1)}{S_r(f, z_1)}\right] \cong -4(z_2 - z_1)(\beta_s - \beta_r)f + \ln[c] \quad [10]$$

The maximum likelihood (ML) estimation of the attenuation coefficient slope $\beta_s$ is $$\beta_{s,ML} = \beta_r + \frac{h_{ML}}{4(z_2 - z_1)}, \quad [11]$$

where $h_{ML}$ is a solution for $$g(h) \stackrel{\Delta}{=} \int_{f_1}^{f_2} (f - f_0) \frac{S_s(f, z_2)}{S_r(f, z_2)} \left[\frac{S_s(f, z_1)}{S_r(f, z_1)}\right]^{-1} \exp[h(f - f_0)] df = 0 \quad [12]$$

and frequency $$f_0 = \frac{f_1 + f_2}{2}.$$

The term $h_{ML}$ can be found iteratively using Newton's method of successive approximation. Given the $n^{th}$ estimate $h_n$, then $$h_{n+1} = h_n - \frac{g(h_n)}{g'(h_n)} = \quad [13]$$

$$h_n - \frac{\int_{f_1}^{f_2} (f - f_0) \frac{S_s(f, z_2)}{S_r(f, z_2)} \left[\frac{S_s(f, z_1)}{S_r(f, z_1)}\right]^{-1} \exp[h_n(f - f_0)] df}{\int_{f_1}^{f_2} (f - f_0)^2 \frac{S_s(f, z_2)}{S_r(f, z_2)} \left[\frac{S_s(f, z_1)}{S_r(f, z_1)}\right]^{-1} \exp[h_n(f - f_0)] df}$$

Figure 2B:
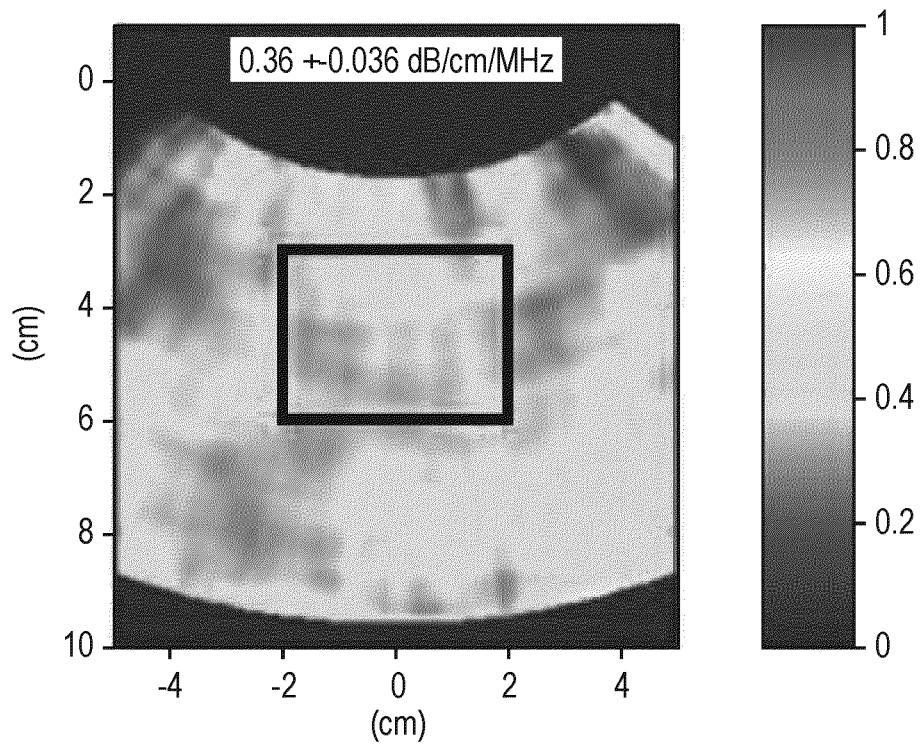

FIG. 2b illustrates an attenuation coefficient slope map produced by the maximum likelihood method.

The foregoing attenuation coefficient mapping techniques show that different methods involve different assumptions. The relative validity of the different assumptions will cause one method to be more accurate for attenuation coefficient estimation than another for a given tissue under analysis. For example, as previously mentioned, when the assumption of homogeneous scatterer distribution over the image field depth is valid, the spectral difference method usually outperforms the maximum likelihood (ML) method in accuracy. It is these differences in accuracy which cause a compounding of maps from different estimation techniques to often be a more accurate realization of attenuation coefficient mapping. In accordance with a further aspect of the present invention, these differences in assumptions and accuracy lead to the ability to characterize an attenuation coefficient map in terms of its confidence or trustworthiness. Maps of confidence factors for the different attenuation coefficient maps are computed by the confidence measure estimator 52 and used to display the confidence in the attenuation coefficients across the image field, or used to compound different attenuation coefficient maps in accordance with their trustworthiness. For instance, for the spectral difference method of attenuation coefficient slope estimation to be accurate, it is necessary for the following expression $$Q(f, z_1, z_2) \equiv \frac{1}{f}\left(\ln\left[\frac{S_s(f, z_2)}{S_r(f, z_2)}\right] - \ln\left[\frac{S_s(f, z_1)}{S_r(f, z_1)}\right]\right) - 4(z_2 - z_1)\beta_r \quad [14]$$

to be independent of f. It will be if $$Q(f, z_1, z_2) \cong \overline{Q}(z_1, z_2) \equiv \frac{\int_{f_1}^{f_2} w(f) Q(f, z_1, z_2) df}{\int_{f_1}^{f_2} w(f) df} \quad [15]$$

It can be determined if this is the case by calculating $$u(z_1, z_2) \equiv \frac{\sqrt{\frac{\int_{f_1}^{f_2} w(f)[Q(f, z_1, z_2) - \overline{Q}(z_1, z_2)]^2 df}{\int_{f_1}^{f_2} w(f) df}}}{|\overline{Q}(z_1, z_2)|}. \quad [16]$$

The confidence in the attenuation coefficient slope estimates is greater when u is smaller and lower when u is larger. A map of u values calculated in this manner for each pixel of an attenuation coefficient slope map calculated by the spectral difference method thus will inform the user of the trustworthiness of the attenuation coefficient slope map and the accuracy of coefficient slope estimations for the ROIs throughout the attenuation coefficient slope map. Differences between a raw attenuation coefficient slope map and its smoothed version (e.g., one which has undergone median filtering) can also be used to indicate confidence, with higher confidence values assigned to pixels with lower differences. Other methods or metrics for deriving confidence measures include texture analysis, flow measurement, tissue response to acoustic radiation force, and coherence in pre-beam-summed channel data. An example of a confidence map of u values for an attenuation coefficient slope map calculated by the spectral difference method for an image field with homogeneous scatterers is illustrated in FIG. 3a, and a confidence map for an attenuation coefficient slope map calculated by the spectral difference method for an image field with scatterer density increasing with depth is illustrated in FIG. 3b. A composite confidence map can be derived from individual confidence maps or measures with proper weighting, together with consideration of consistency across different attenuation coefficient maps. For example, when the attenuation coefficient estimates from different methods for a pixel differ significantly from each other, the consistency is considered low, and such information will be used to adjust the confidence level or weighting of different methods for that pixel for a final attenuation coefficient map.

The attenuation coefficient map compounder 54 produces a final attenuation coefficient map by compounding attenuation coefficient maps produced by different methods. During compounding, an attenuation coefficient (slope) map with higher confidence values and/or higher consistency with other maps will be given larger weights in the combining process. For instance, if an attenuation coefficient from one map for a given pixel has a higher confidence value than the coefficients from the other maps, that coefficient value will be given greater weight than the others in the combining process. If the attenuation coefficients from two of the maps have a higher consistency than the attenuation coefficient from a third map, e.g., are within 5% of each other, whereas the value from the third map differs by 20% from the others, then the coefficients from the first two maps would be given greater weights in the combining process. Compounding of the different maps proceeds in this manner on a pixel-by-pixel basis until a final attenuation map has been produced for display to the user. As previously mentioned the final map can be displayed alone, or in conjunction with one or all of the confidence maps or, preferably, in conjunction with a consolidated confidence map.

It is understood that the elements features in FIG. 1, e.g. beamformer, signal processor, QEP, beamform controller, graphics processor, attenuation coefficient map compounder, confidence measure estimator, attenuation coefficient estimator, b-mode processor, doppler processor, scan convertor, image memory, volume render, and display processor, may be formed from one or more combination of processors that are executing instructions included on one or more memories associated with the processors. It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system and its controller, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as a memory for the reference value map for the attenuation coefficient estimator 50 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine. The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. The equations given above for the different methods for attenuation coefficient estimation and mapping, as well as the calculations used to produce the confidence maps described above, are typically calculated by or under the direction of software routines. Further, the software may be in the form of a collection of separate programs or modules such as an attenuation coefficient computing module, or an attenuation coefficient mapping program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

The invention claimed is:

1. An ultrasound imaging system which produces attenuation coefficient maps of an image field comprising:
   an ultrasound probe adapted to acquire ultrasonic echo signals from the image field;
   a beamformer adapted to process the ultrasonic echo signals to produce coherent echo signals for an ultrasound image of the image field;
   an attenuation coefficient estimator, coupled to the beamformer, and adapted to estimate attenuation coefficient values for maps of attenuation coefficients of the image field, characterized in that:
   the attenuation coefficient estimator is further adapted to produce a plurality of attenuation coefficient maps by two or more of the methods of a spectral difference method, a spectral log difference method, and a maximum likelihood method;
   the system comprises an attenuation coefficient map compounder, coupled to the attenuation coefficient estimator, and adapted to compound the plurality of attenuation coefficient maps produced by said two or more different attenuation coefficient estimation methods; and
   the system comprises a display adapted to display attenuation coefficient maps produced by the attenuation coefficient map compounder.

2. The ultrasound imaging system of claim 1, wherein the coefficient maps are color-coded.

3. The ultrasound imaging system of claim 1, wherein the spectral difference method is adapted to assume homogeneous scatterer distribution over the image field depth.

4. The ultrasound imaging system of claim 1, wherein the maximum likelihood method is adapted to handle nonuniform scatterer distribution over the image field depth.

5. The ultrasound imaging system of claim 1, wherein the attenuation coefficient map compounder is further adapted to compound two or more of the attenuation coefficient maps produced by the attenuation coefficient estimator on a pixel-by-pixel basis.

6. The ultrasound imaging system of claim 5, wherein the attenuation coefficient map compounder is further adapted to compound two or more of the attenuation coefficient maps produced by the attenuation coefficient estimator by weighted averaging.

7. The ultrasound imaging system of claim 6, wherein the attenuation coefficient map compounder is further adapted to compound two or more of the attenuation coefficient maps using weights determined by confidence estimations.

8. The ultrasound imaging system of claim 6, wherein the attenuation coefficient map compounder is further adapted to compound two or more of the attenuation coefficient maps using weights determined by attenuation coefficient consistency of the maps being compounded.

9. The ultrasound imaging system of claim 1, further comprising a confidence measure estimator, coupled to the attenuation coefficient estimator, which is adapted to produce a map of confidence estimations corresponding to an attenuation coefficient map.

10. The ultrasound imaging system of claim 9, wherein the attenuation coefficient map compounder is further adapted to compound two or more of the attenuation coefficient maps using weights determined in consideration of the map of confidence estimations.

11. The ultrasound imaging system of claim 9, wherein the display is further adapted to display the map of confidence estimations.

12. The ultrasound imaging system of claim 1, further comprising a memory adapted to store a map of reference values, and the attenuation coefficient estimator is adapted to operate on RF echo signal data values or I/O echo signal data, in conjunction with the map of reference values,
wherein the reference values comprise power spectrum measurements of a tissue phantom.

13. The ultrasound imaging system of claim 1, further comprising a memory adapted to store a map of reference values, and the attenuation coefficient estimator is adapted to operate on RF echo signal data values or I/O echo signal data, in conjunction with the map of reference values,
wherein the reference values comprise a theoretical model of power spectra, or a numerical simulation of power spectra.

* * * * *